(12) United States Patent
Gerbec et al.

(10) Patent No.: US 6,648,917 B2
(45) Date of Patent: Nov. 18, 2003

(54) ADJUSTABLE BONE FUSION IMPLANT AND METHOD

(75) Inventors: Daniel E. Gerbec, Logan, UT (US); T. Wade Fallin, Hyde Part, UT (US); Tom Faciszewski, Marshfield, WI (US)

(73) Assignees: MedicineLodge, Inc., Logan, UT (US); Movdicé Holding, Inc., Boulder City, NV (US)

( * ) Notice: Subject to any disclaimer, the term of this patent is extended or adjusted under 35 U.S.C. 154(b) by 0 days.

(21) Appl. No.: 09/981,674

(22) Filed: Oct. 17, 2001

(65) Prior Publication Data

US 2003/0074063 A1 Apr. 17, 2003

(51) Int. Cl.⁷ .................................................. A61F 2/44
(52) U.S. Cl. .............................. 623/17.11; 623/17.15
(58) Field of Search ........................... 623/17.11, 17.15, 623/17.16

(56) References Cited

U.S. PATENT DOCUMENTS

| | | | |
|---|---|---|---|
| 4,657,550 A | 4/1987 | Daher |
| 4,834,757 A | 5/1989 | Brantigan |
| 4,863,476 A | 9/1989 | Shepperd |
| 5,059,193 A | 10/1991 | Kuslich |
| 5,171,278 A | 12/1992 | Pisharodi |
| 5,290,312 A | 3/1994 | Kojimoto et al. |
| 5,306,310 A | 4/1994 | Siebels |
| 5,336,223 A | 8/1994 | Rogers |
| 5,390,683 A | 2/1995 | Pisharodi |
| 5,405,391 A | 4/1995 | Hednerson et al. |
| 5,425,772 A | 6/1995 | Brantigan |
| 5,443,514 A | 8/1995 | Steffee |
| 5,458,641 A | 10/1995 | Ramirez Jimenez |
| 5,554,191 A | 9/1996 | Lahille et al. |
| 5,571,192 A | 11/1996 | Schonhoffer |
| 5,653,762 A | 8/1997 | Pisharodi |
| 5,653,763 A | 8/1997 | Errico et al. |
| 5,658,335 A | 8/1997 | Allen |
| 5,665,122 A | 9/1997 | Kambin |
| 5,693,100 A | 12/1997 | Pisharodi |
| 5,702,455 A | 12/1997 | Saggar |

(List continued on next page.)

*Primary Examiner*—Eduardo C. Robert
*Assistant Examiner*—David A Bonderer
(74) *Attorney, Agent, or Firm*—Workman Nydegger

(57) ABSTRACT

An adjustable bone fusion implant includes a first plate having an interior face with a plurality of spaced apart first support members projecting therefrom. Each support member has a plurality of teeth projecting therefrom. A second plate has an interior face with a plurality of spaced apart second support members projecting therefrom. Each second support member has at least one tooth projecting therefrom. At least a portion of the plurality of teeth of each first support member mechanically engages with the at least one tooth of a corresponding second support member so that the first plate and the second plate can be selectively separated while forming a compartment therebetween. A reinforcing member is disposed between the first plate and the second plate such that the application of a compressive force between the first plate and the second plate applies compression on the reinforcing member.

10 Claims, 13 Drawing Sheets

U.S. PATENT DOCUMENTS

| | | |
|---|---|---|
| 5,716,415 A | 2/1998 | Steffee |
| 5,776,198 A | 7/1998 | Rabbe et al. |
| 5,782,832 A | 7/1998 | Larsen et al. |
| 5,865,848 A | 2/1999 | Baker |
| 5,980,522 A | 11/1999 | Koros et al. |
| 5,989,290 A | 11/1999 | Biedermann et al. |
| 6,015,436 A | 1/2000 | Schonhoffer |
| 6,045,579 A | 4/2000 | Hochshuler et al. |
| 6,080,193 A | 6/2000 | Hochshuler et al. |
| 6,093,207 A | 7/2000 | Pisharodi |
| 6,102,950 A * | 8/2000 | Vaccaro ............... 623/17.16 |
| 6,117,174 A | 9/2000 | Nolan |
| 6,126,689 A | 10/2000 | Brett |
| 6,126,869 A | 10/2000 | Haaland |
| 6,129,763 A | 10/2000 | Chauvin et al. |
| 6,159,244 A * | 12/2000 | Suddaby ............... 623/17.11 |
| 6,174,334 B1 | 1/2001 | Suddaby |
| 6,176,881 B1 | 1/2001 | Schar et al. |
| 6,183,517 B1 | 2/2001 | Suddaby |
| 6,190,413 B1 | 2/2001 | Sutcliffe |
| 6,190,414 B1 | 2/2001 | Young et al. |
| 6,193,755 B1 | 2/2001 | Metz-Stavenhagen et al. |
| 6,193,756 B1 | 2/2001 | Studer et al. |
| 6,193,757 B1 | 2/2001 | Foley et al. |
| 6,200,348 B1 | 3/2001 | Biedermann et al. |
| 6,296,647 B1 * | 10/2001 | Robioneck et al. ......... 606/105 |
| 6,299,644 B1 | 10/2001 | Vanderschot |
| 6,332,895 B1 | 12/2001 | Suddaby |
| 6,395,034 B1 * | 5/2002 | Suddaby ............... 623/17.15 |
| 6,419,705 B1 | 7/2002 | Erickson |
| 2001/0032017 A1 | 10/2001 | Alfaro et al. |
| 2002/0010511 A1 | 1/2002 | Michaelson |

* cited by examiner

ADJUSTABLE BONE FUSION IMPLANT AND METHOD

CROSS-REFERENCE TO RELATED APPLICATIONS

Not applicable.

BACKGROUND OF THE INVENTION

1. The Field of the Invention

The present invention relates generally to surgical devices and methods for fusing adjacent bone structures and, more specifically, to surgical devices and methods for fusing adjacent vertebrae.

2. The Relevant Technology

The spinal column is made up of thirty-three vertebra each separated by a cushioning disc. Disease and trauma can damage these discs, creating instability that leads to loss of function and excruciating pain. Spinal fusion implants provide a successful surgical outcome by replacing the damaged disc and restoring the spacing between the vertebra, eliminating the instability and removing the pressure on neurological elements that cause pain. The fusion is accomplished by providing an implant which recreates the natural intervertebral spacing and which has an internal cavity with outwardly extending openings. The internal cavity is commonly filled with osteogenic substances, such as autogenous bone graft or bone allograft, to cause the rapid growth of a bony column through the openings of the implant.

Recently, adjustable fusion implants have been developed that allow the surgeon to adjust the height of the implant. This provides an ability to intra-operatively tailor the implant height to match the natural spacing between the vertebrae. This reduces the number of sizes that the hospital must keep on hand to match the variable anatomy of the patients. However, the prior art is replete with adjustable fusion implants that have an active mechanism for expanding the implant to change its height. Active mechanism refers to a mechanical structure built into the implant to cause the change in the height dimension. The presence of the active mechanism significantly decreases the amount of internal space available for placement of bone graft and other osteogenic substances to encourage the bony fusion between the adjacent vertebrae. It would therefore be an improvement over the prior art to provide an adjustable fusion implant that does not require the presence of an active mechanism, thereby maximizing the internal space for osteogenic substances and providing a better inducement for bony fusion.

Other adjustable fusion implants known in the art are comprised of modular components that must be pre-assembled prior to implantation. It would therefore be an advantage to provide a fusion implant that can be adjusted in situ.

Another challenge associated with spinal fusion is the restoration of the curvature of the spine. This curvature is present at each intervertebral level at varying degrees, and is manifested by a different spacing or height at the anterior and posterior margins of adjacent vertebral bodies. For example, the lumbar spine has a natural curvature when viewed from a lateral perspective referred to as lordosis, where the mid section of the lumbar spine is more anterior than the end sections. Thus, at any given intervertebral level, the intervertebral height at the posterior margin is less then the intervertebral height at the anterior margin, resulting in a wedge shaped disc or intervertebral space.

When a spinal fusion implant is placed from the posterior aspect of the vertebra, it must be sized to fit through the smaller posterior space, resulting in an undersized fit at the anterior end once the implant is in place. When the vertebral bodies are made to contact the opposing surfaces of the fusion implant, the curvature of the spine is straightened, producing higher stresses in adjacent levels of the spinal column and potentially leading to faster degeneration of adjacent intervertebral discs. Because some clinical problems require surgery from the posterior approach, it would be desirable to install an intervertebral fusion implant from the posterior side of the patient. It would therefore be an improvement to provide a spinal fusion implant that could recreate the natural curvature of the spine by reproducing the wedge shaped intervertebral space and concurrently allow for installation from the narrow side of the intervertebral space.

BRIEF SUMMARY OF THE INVENTION

The present invention provides an adjustable bone fusion implant for selectively fusing together bones and/or pieces of bone. Methods are also disclosed for using and assembling the fusion implant. In one embodiment, the adjustable bone fusion implant comprises a first plate having an interior face and an opposing exterior face. Four spaced apart first support members project from the interior face of the first plate, each first support member having a rack of teeth projecting therefrom.

The fusion implant further comprises a second plate having an interior face and an opposing exterior face. The interior face of the first plate faces the interior face of the second plate such that a compartment is formed therebetween. Four second support members project from the interior face of the second plate. Each second support member has at least one tooth projecting therefrom.

The rack of teeth on each first support member mesh with the at least one tooth of a corresponding second support member. The meshed teeth enable selective separation of the first plate and the second plate but preclude unwanted collapsing between the plates. A plurality of grafting ports extend through each of the first and second plates so as to communicate with chamber. The grafting ports facilitate growth of bone through the fusion implant. A plurality of retention barbs outwardly project from the exterior face of the first and second plate. The retention barbs engage with the bone to be fused so as to help minimize migration or movement of the fusion implant.

Once the fusion implant has been expanded to fit a desired space, a reinforcing member can be inserted between the first plate and the second plate. The reinforcing member is positioned such that any compression load applied to the fusion implant is primarily carried through the reinforcing member as opposed to being carried between the meshed teeth. As a result, use of the reinforcing member substantially increases the amount of compression load that the fusion implant can bear prior to failure or permanent deformation.

In one embodiment, the fusion implant has a wedged shaped configuration so that it can be appropriate fit within a wedged shaped opening. For example, such wedged shaped fusion implants can be inserted between adjacent vertebrae.

In further accordance with the present invention, there is provided a method of installing the adjustable fusion implant. The components are first assembled in a fully collapsed state and connected to both an inserter and a distraction tool. The fusion implant is then placed between bones or bone parts to be fused. In the method discussed below, the fusion implant is inserted into an intervertebral space. The inserter is generally in the form of a solid rod. In one method, the fusion implant can be independently placed into the desired space by the inserter. The distraction tool can then be delivered to the fusion implant by referencing the inserter rod. In its collapsed state, the insertion profile of the fusion implant is less than the minimal spacing between the adjacent vertebrae. For lumbar spine applications, it is noted that the posterior spacing is less than the anterior spacing due to the spine curvature, or lordosis.

Next, the fusion implant is expanded by applying a distraction force from the distraction tool. The distraction force causes the meshed teeth on the support members to advance one tooth spacing at a time. Once the fusion implant is expanded to the size of the intervertebral space, the distraction tool is removed.

The next operative step is the introduction of the reinforcing member. The reinforcing member is aligned with or attached to a tubular push rod which in turn is advanced over the inserter. As the push rod is advanced, the reinforcing member is pushed into position between the first and second plates of the fusion implant. Once the reinforcing member is placed in its final assembled position, the inserter is removed. With the push rod still attached to the implant, the tubular push rod provides a channel in fluid communication with the chamber of the fusion implant. The channel can be use to deliver osteogenic substance, such as bone graft, to the compartment to facilitate bone growth. Once the osteogenic substance is delivered, the push rod can be removed. The completed operative technique provides restoration of the intervertebral spacing and restoration of the natural curvature of the spine through an approach from either the wide or narrow side of the intervertrebral spacing.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Figure 1:
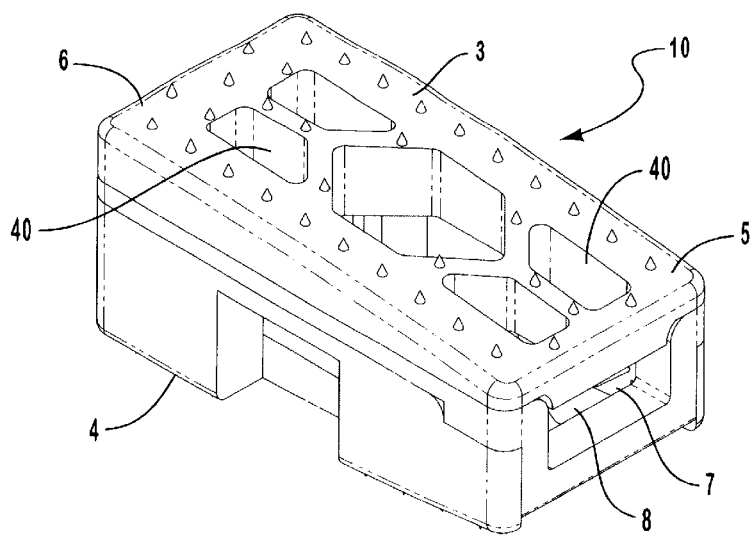
FIG. 1 is a perspective view of one embodiment of an adjustable bone fusion implant in an assembled state.

Depicted in FIG. 1 is one embodiment of an inventive adjustable bone fusion implant 10 incorporating features of the present invention. Fusion implant 10 is designed for placement between bones and/or pieces of bone to facilitate fusing of the bone matter together. Considered as a whole, in the embodiment depicted fusion implant 10 has a substantially rectangular box shaped configuration with a top surface 3 and an opposing bottom surface 4 that extend between a proximal end 5 and an opposing distal end 6. Fusion implant 10 has an interior surface 7 that bounds a compartment 8. A plurality of grafting ports 40 extend through fusion implant 10 so as to communicate with compartment 8. Either before, during, and/or after positioning of fusion implant 10 between bone matter, compartment 8 is at least partially packed with an osteogenic substance, such as autogenous bone graft or bone allograft. Once fusion implant 10 is disposed between the bone matter, the osteogenic substance causes the rapid growth of a bony column through grafting ports 40, thereby forming the bone matter into a solid continuous bone.

In the embodiment depicted, fusion implant 10 has a substantially wedged shaped configuration. That is, the height of fusion implant 10 at proximal end 5 is shorter than the height at distal end 6. The wedged shaped configuration facilitates placement of fusion implant 10 in wedged shaped openings such as between select vertebrae for fusing the vertebrae together. In alternative embodiments, it is appreciated that fusion implant 10 can be configured at any desired wedge angle or can have substantially parallel top and bottom surfaces. Furthermore, fusion implant 10 need not have a rectangular box shaped configuration but can be square, circular, or have any other polygonal or irregular configuration.

Figure 2:
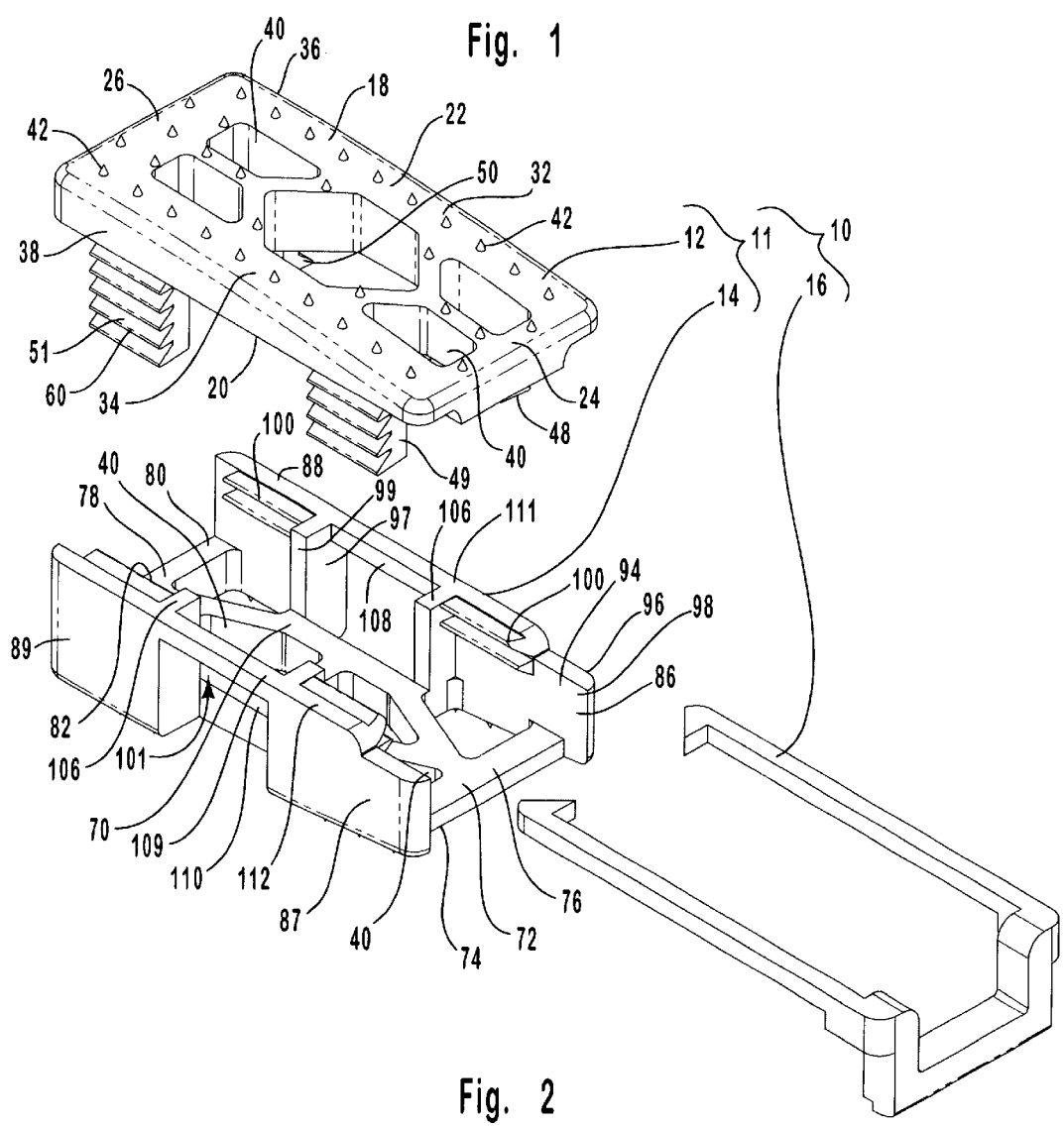
FIG. 2 is a perspective view of the embodiment shown in FIG. 1 in a disassembled state.

As depicted in FIG. 2, fusion implant 10 comprises a housing 11 and a reinforcing member 16. Housing 11 comprises a cap 12 that is selectively connected to a base 14. Cap 12 comprises a cap plate 18 having an interior face 20 an opposing exterior face 22 that each extend between a proximal end 24 and an opposing distal end 26. The term "plate" as used in the specification and appended claims is broadly intended to include not only structures that have a flat or substantially flat surface but also, for example, members that are curved, sloped, have regular or irregular formations thereon, and have openings extending therethrough.

Figure 3A:
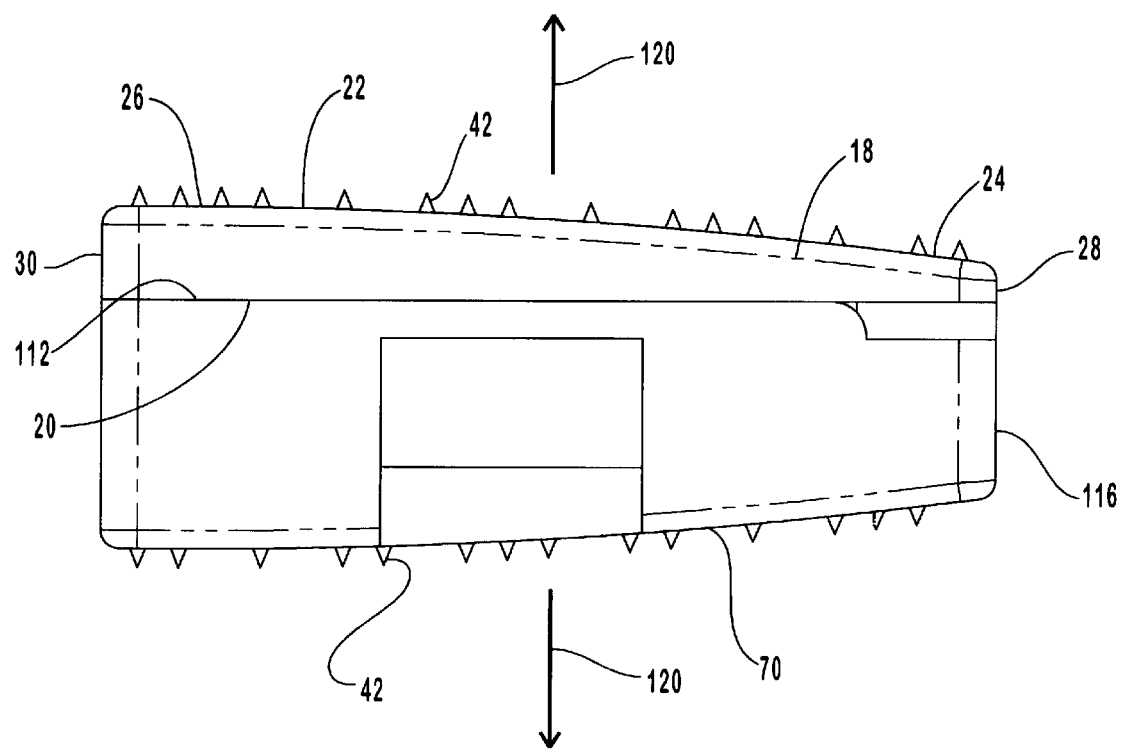
FIG. 3A is an elevated side view of the housing of the embodiment shown in FIG. 1 in a fully collapsed state.
Figure 3B:
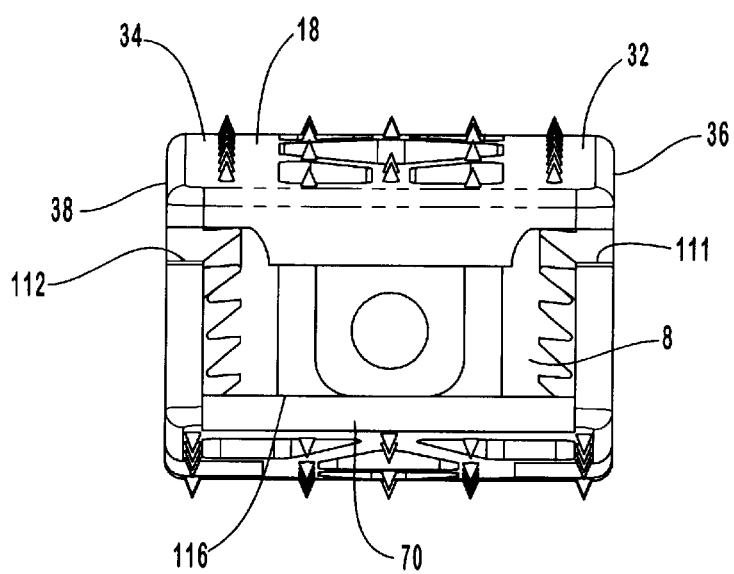
FIG. 3B is an elevated front end view of the embodiment shown in FIG. 3A.

As shown in FIG. 3A, proximal end 24 of cap plate 18 terminates and an end face 28 while distal end 26 terminates at a distal end face 30. Exterior face 22 is sloped relative to interior face 20 such that cap plate 18 has a wedged shaped configuration with end face 28 being shorter than end face 30. In alternative embodiments, either or both of faces 20 and 22 can be sloped or both horizontally disposed in parallel alignment. As depicted in FIGS. 2 and 3B, faces 20 and 22 also extend between opposing sides 32 and 34. Sides 32 and 34 terminate at side faces 36 and 38, respectively.

Extending through cap plate 18 from exterior face 22 to interior face 20 are a plurality of grafting ports 40. In one embodiment grafting ports 40 comprise about 25 percent to about 50 percent and more commonly about 25 percent to about 35 percent of the surface area of exterior face 22 of cap plate 18 that contacts bone. In alternative embodiments, it is appreciated that any number of grafting ports 40 can be used and that each grafting port can have any desired configuration or size. It is also appreciated that cap plate 18 can be formed with no grafting ports 40 extending therethrough.

Upwardly projecting from exterior face 22 of cap plate 18 are a plurality of retention barbs 42. Retention barbs 42 function to frictionally engage with adjacent bone so as to enhance fixation and resist implant migration or movement of fusion implant 10 relative to the bone. In alternative embodiments, it is appreciated that any number of one or more retention barbs 42 can be mounted on cap plate 18 and that barbs 42 can have any desired configuration so as to effectively engage with bone. For example, in alternative embodiments barbs 42 can comprise discrete teeth or aligned racks of teeth. It is also appreciated that barbs can be oriented at a common or at different angles so as to more effectively prevent movement in a specific direction.

Figure 4A:
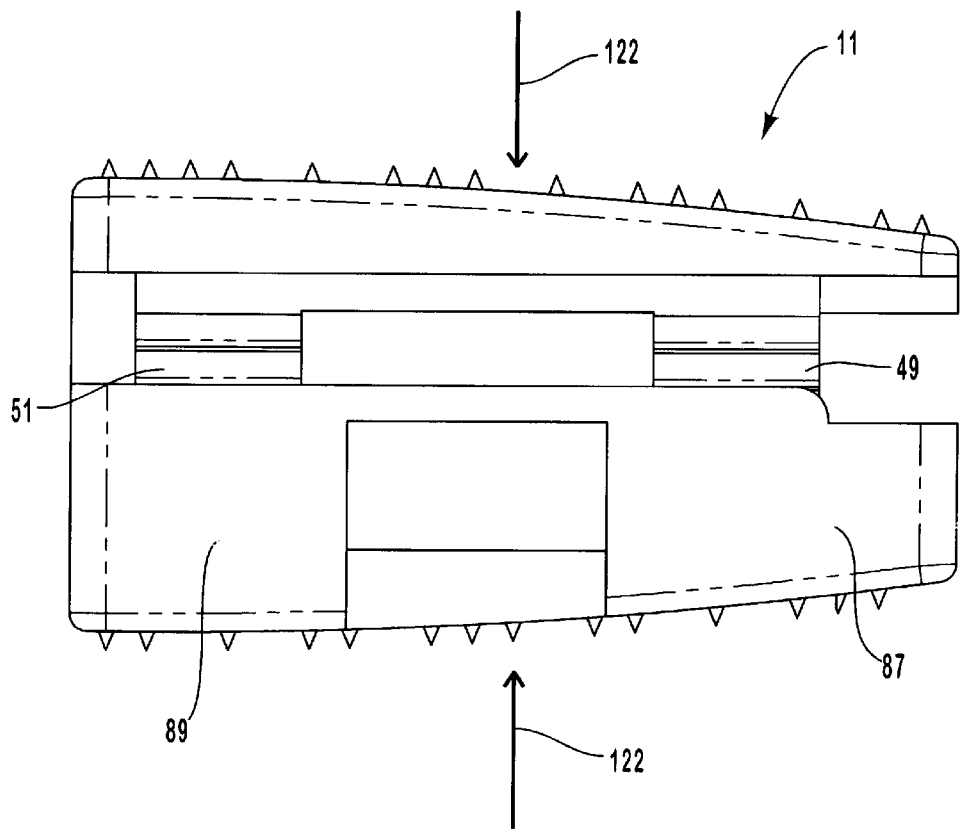
FIG. 4A is an elevated side view of the embodiment shown in FIG. 3A in a partially expanded state.
Figure 4B:
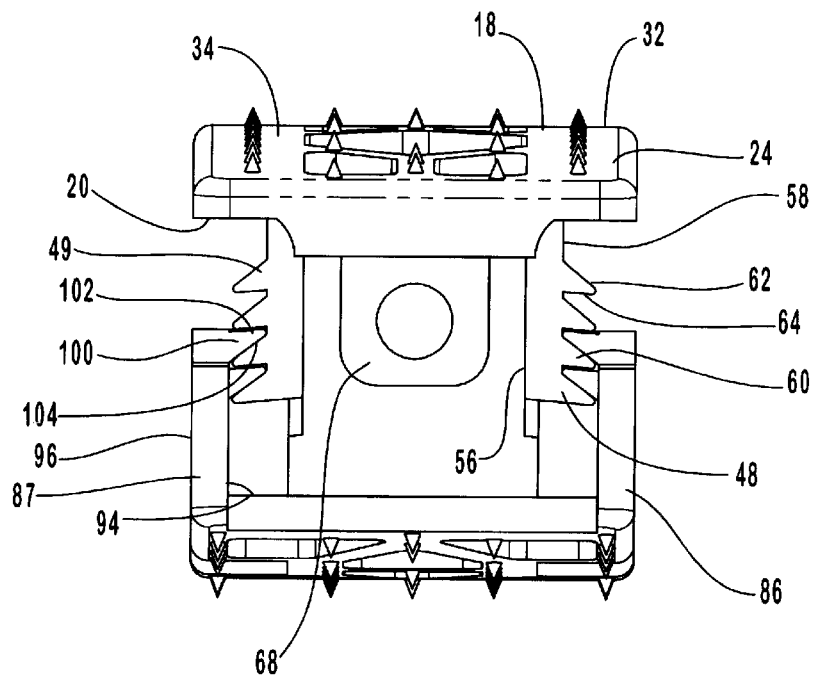
FIG. 4B is an elevated front end view of the embodiment shown in FIG. 4A.

As perhaps best depicted in FIGS. 2, 4A, and 4B, a plurality of support members downwardly project from interior face 20 of cap plate 18. More specifically, a first pair of spaced apart support members 48 and 49 downwardly project along sides 32 and 34 of cap plate 18 at proximal end 24. Similarly, a pair of spaced apart support members 50 and 51 downwardly project along sides 32 and 34 of cap plate 18 at distal end 26. As shown in FIG. 4B each support member has an inside face 56 and an outside face 58. Outwardly projecting on outside face 58 is a rack or plurality of teeth 60. Each tooth 60 has a downwardly sloping top surface 62 and a substantially horizontally disposed bottom surface 64.

In one embodiment, teeth 60 have a spacing in a range between about 0.5 mm to about 2 mm and more commonly in a range between about 0.5 mm to about 1 mm. In alternative embodiments, teeth 60 can be spaced at any desired increments.

Figure 4C:
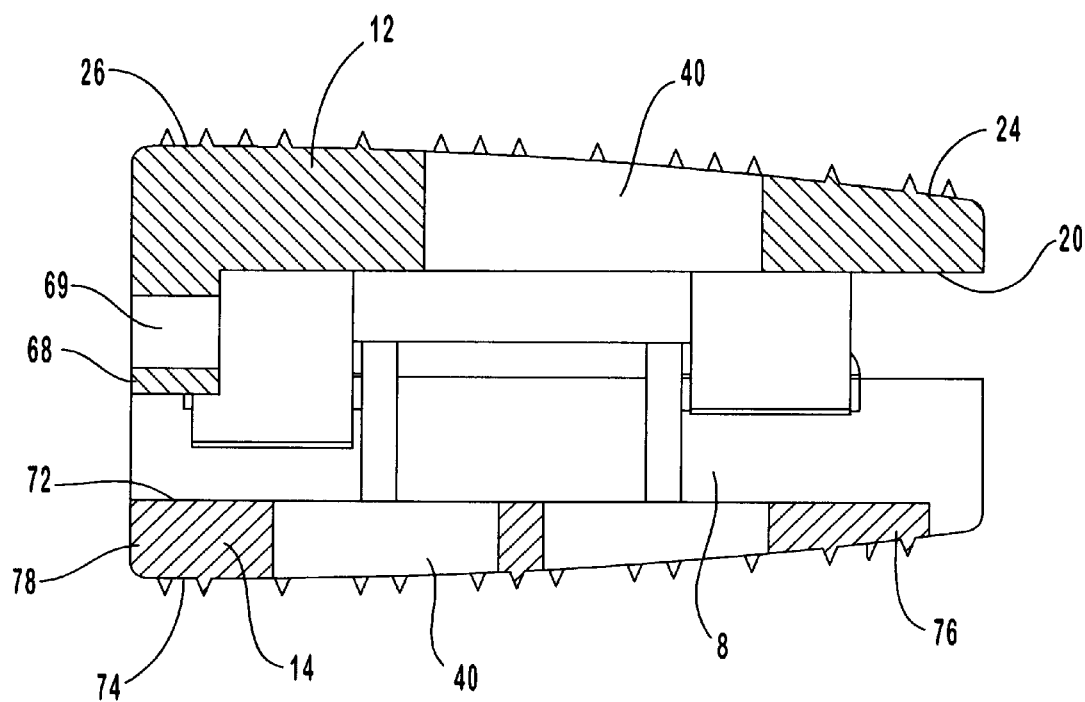
FIG. 4C is a cross sectional side view of the embodiment shown in FIG. 4A.

As depicted in FIGS. 4B and 4C, an attachment flange 68 downwardly projects from interior face 20 of cap plate 18 at distal end 26. For reasons as will be discussed later in great detail, a threaded aperture 70 extends through attachment flange 68. In this configuration, threaded aperture 69 communicates with compartment 8 within fusion implant 10.

Returning to FIG. 2, base 14 includes a base plate 69 that is comparable to cap plate 18. That is, base plate 70 also includes an interior face 72 and an exterior face 74 that each extend between a proximal end 76 and an opposing distal end 78. Faces 72 and 74 likewise extend between opposing sides 80 and 82. Extending through base plate 70 between interior face 72 and exterior face 74 are a plurality of grafting ports 40. The grafting ports in base plate 70 can be positioned in the same alternative number, size, and configuration as discussed above with regard to the grafting ports in cap plate 18. Outwardly projecting from exterior face 74 are a plurality of retention barbs 42. Retention barbs 42 on base plate 70 can also have the same alternative size, configuration, and orientation as retention barbs 42 on cap plate 18.

As depicted in FIG. 4C, exterior face 74 of base plate 70 is sloped relative to interior face 72 so that base plate 70 is thicker at distal end 78 than at proximal end 76. As with cap plate 18, base plate 70 can also have a constant thickness with both faces 72 and 74 being either sloped or horizontally disposed. Furthermore, each of faces 72 and 74 can be sloped at different angles. Although not required, in the embodiment depicted interior face 72 of base plate 70 is disposed substantially parallel to interior face 20 of cap plate 18. As previously discussed, in alternative embodiments it is appreciated that only one of exterior faces 22 and 74 can be sloped or, if desired, neither face can be sloped.

Returning to FIG. 2, a plurality of support members also upwardly extend from base plate 70. Specifically, a pair of spaced apart support members 86 and 87 upwardly extend from sides 80 and 82, respectively, of base plate 70 at proximal end 76. Similarly, a pair of spaced apart support members 88 and 89 upwardly project from sides 80 and 82, respectively, of base plate 70 at distal end 78. As depicted in FIG. 2, each support member 86–89 of base plate 70 has an inside face 94 and an opposing outside face 96 that each extend to a free top end 98. Extending between support members 86 and 88 at top end 98 is a brace 108. Brace 108 and support members 86 and 88 form an exposed biasing rail 111 that runs the length of side 80 of base plate 70. A brace 109 extends between support members 87 and 89 at top ends 98 thereof. Brace 109 and support members 87 and 89 form an exposed biasing rail 112 that runs the length of side 82 of base plate 70. Formed below each brace 108 and 109 is a side port 110 that communicates with compartment 8. In part, each side port 110 acts as a grafting port to facilitate bone growth.

Inwardly projecting from inside face 94 at top end 98 of each support member 86–89 are a pair of adjacently disposed teeth 100. As seen in FIG. 4B, each tooth 100 has a horizontally disposed top surface 102 and an upwardly slopping bottom surface 104. Returning to FIG. 2, a retention wall 106 inwardly projects from each support member 86–89 between teeth 100 and side ports 110. As discussed later in greater detail, each retention wall 106 function as a stop.

Each retention wall 106 has an inside face 97 that extends to an end face 99. Each inside face 97 faces one of side ports 110. It is noted that at each side port 110, base plate 70 extends only to end face 99 of each retention wall 106. Furthermore, braces 108 and 109 only extend part way toward end face 99 of retention walls 106. As such, there is an open vertical channel 101 formed between each pair of adjacent retention walls 106. Each vertical channel 101 extends along the height of inside face 97 of retention walls 106 adjacent to where each inside faces 97 intersects with end face 99. As such, the top of each vertical channel 101 is located inside of braces 108 and 109. As discussed later in greater detail, vertical channels 101 can be used for the initial attachment of cap 12 to base 14.

The above described cap 12 and base 14 are configured for mechanical mating. Specifically, as depicted in FIGS. 2A and 2B, cap 12 is configured to mate with base 14 such that interior face 20 of cap plate 18 can selectively rest on biasing rails 111 and 112 of base 14. In this configuration, teeth 60 on support members 49–51 of cap 12 complementary mesh with teeth 100 on corresponding support members 86–89 of base 14. In this assembled configuration, compartment 8 is formed between cap plate 18 and base plate 70. An access mouth 116 is formed at the proximal end of assembled housing 11 and provides access to compartment 8.

As a separation force is applied to cap 12 and base 14 in the directions indicated by arrows 120 in FIG. 3A, the complementary upwardly sloping surfaces 62 and 104 on teeth 60 and 100 create an inward flexing movement of support members 48–51 on cap 12 and/or an outward flexing movement of support members 86–89 on base 14. This flexing of the support members enables the teeth to ride over each other. As a result, as depicted in FIGS. 4A and 4B, housing 11 can be selectively expanded by predefined incremental amounts. The incremental amounts are based on the spacing of the teeth.

In contrast, as a compression force is applied to cap 12 and base 14 in the directions indicated by arrows 122 depicted in FIG. 4A, the mating horizontal surfaces 64 and 102 of teeth 60 and 100 press against one another so as to substantially preclude the collapse of housing 11. Any compression of housing 11 is due either to elastic compression of the material or failure of housing 11. It is appreciated that retention walls 106 preclude horizontal sliding between cap 12 and base 14 when they are secured together. That is, support members 48–51 and/or teeth 60 thereon of cap 12 bias against retention walls 106, which act as a stop, when any transverse force is applied so as to attempt to horizontally separate cap 12 and base 14.

In one embodiment of the present invention, means are provided for mechanically connecting cap plate 18 to base plate 70 such that cap plate 18 and base plate 70 can be selectively manually separated so as to enlarge the size of compartment 8. By way of example and not by limitation, one embodiment of such means comprises support members 48–51 and 86–89 with interacting teeth 60 and 100 as described above.

In alternative embodiments, it is appreciated that the orientation of the various support members and their corresponding teeth can be reversed between cap 12 and base 14. It is also appreciated, that each of teeth 60 and 100 can each be formed in various combinations of one or more teeth. Furthermore, rather than having four support members on each of cap plate 18 and base plate 70, it is appreciated that a single elongated support member can be centrally disposed on each side of cap plate 18 and base plate 70. In this embodiment, a retention wall is mounted on each opposing end of each support member on one plate so as to prevent sliding movement therebetween.

In yet another embodiment, for reasons as will become apparent below, it is also envisioned that teeth 60 and 100 can be formed with a sloping face on each side such that cap plate 18 and base plate 70 can be selectively separated by the application of the separation force and selectively collapsed by the application of the compression force 122. Furthermore, teeth 60 and 100 can have a variety of other conventional configurations which would enable the teeth to mesh together and still enable selective separation of cap plate 18 and base plate 70.

In one embodiment housing 11 depicted in FIGS. 4A and 4B can withstand a compression force 122 of over 400 pounds without failure or producing permanent deformation. As such, depending on the intended use, housing 11 can independently comprise fusion implant 10. In other situations, however, it is desirable that housing 11 be able to withstand a significantly greater compressive force 122 prior to failure or permanent deformation. In such situations, reinforcing member 16 is used.

Figure 5A:
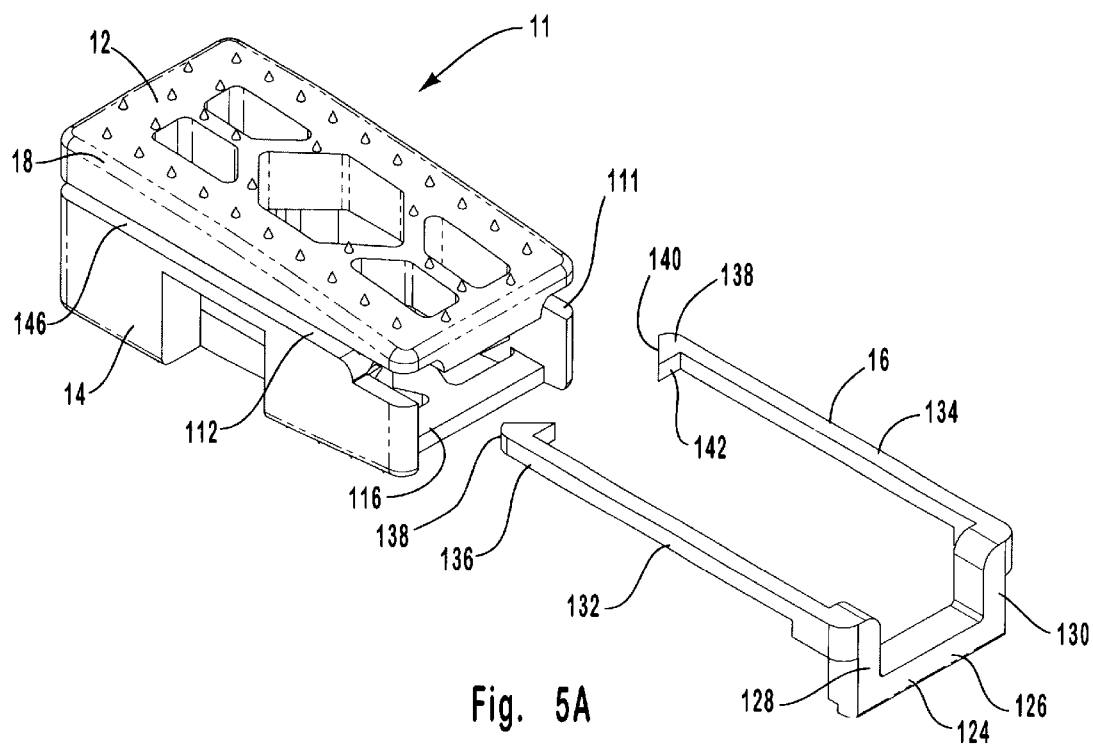
FIG. 5A is a perspective view of the partially expanded fusion implant shown in FIG. 4A configured to receive a reinforcing member.

As depicted in FIG. 5A, reinforcing member 16 is in the form of a substantially U-shaped clip. Specifically, reinforcing member 16 comprises a substantially U-shaped cantilever beam 124 which includes an elongated base 126 having supports 128 and 130 upstanding from each opposing end thereof. Forwardly projecting from the top end of support 128 and 130 is an elongated flexible arm 132 and 134, respectively. Each arm 132 and 134 terminates at a free end 136 having an inwardly facing latching barb 138 formed thereat. Each latching barb 138 has a sloped forward surface 140 and an orthogonally disposed inside surface 142. Reinforcing member 16 has a width extending between the outside of opposing arms 132 and 134 that is substantially the same as the maximum width of cap 12 and base 14.

Once cap 12 is selectively elevated relative to base 14, a gap 146 is formed between cap plate 18 and each biasing rail 111 and 112. Reinforcing member 16 is configured such that each arm 132 and 134 can be slidably received within a corresponding gap 146 on each side of housing 11. Sloping surface 140 on each latching barb 138 biases against support members 48–51 and/or the threads thereon causing arms 132, 134 and/or cantilever beam 124 to outwardly bend, thereby enabling latching barbs 138 to pass over support members 48–51. As latching barbs 138 pass over support members 50 and 51, the resilient flexing of arms 132, 134 causes latching barbs 138 to inwardly bias and catch behind support members 50 and 51. The engagement of flat inside surface 142 of each latching barb 138 against the flat side of support members 50 and 51 prevents reinforcing member 116 from unintentionally disconnecting with housing 15.

In this assembled configuration, the compressive force 122 applied to the assembled fusion implant 10 causes arms 132 and 134 of reinforcing member 16 to be compressed between cap plate 18 and biasing rails 111 and 112. As a result, the compressive load is carried primarily through reinforcing member 16 as opposed to through interlocking teeth 60 and 100. In such configuration, some embodiments of fusion implant 10 are capable of withstanding over 2,000 pounds of compressive force without failure or permanent deformation.

As previously discussed, gap size 146 can be selectively incrementally increased by adjusting which teeth 60 and 100 are meshed together. In one embodiment, a discrete reinforcing member is provided for each gap size 146. For example, depicted in FIGS. 5A and 5B, reinforcing member 16 is configured to be received within gap 146 so as to produce a relatively close tolerance. Depicted in FIGS. 6A and 6B, a gap 150 is formed between cap plate 18 and biasing rails 111 and 112. Gap 150 has a height greater than the height of gap 146. For example, gap size 146 may correspond to a single tooth spacing while gap 150 corresponds to a spacing of two or more teeth. As such, a reinforcing member 152 is provided. Although reinforcing member 152 has the same structural elements as reinforcing member 16, arms 132 and 134 thereof have an increased height so as to selectively receive within gap 150 under a relatively close tolerance. It is appreciated that a plurality of reinforcing members can be provided with each reinforcing member being configured to fit a different sized gap formed between cap plate 18 biasing rails 111 and 112. In an alternative embodiment, it is also appreciated that instead of using a larger reinforcing member, a plurality of smaller reinforcing members could be used to fill a single gap. This would minimize the requirement of having to maintain a number of different sizes of reinforcing members.

Figure 5B:
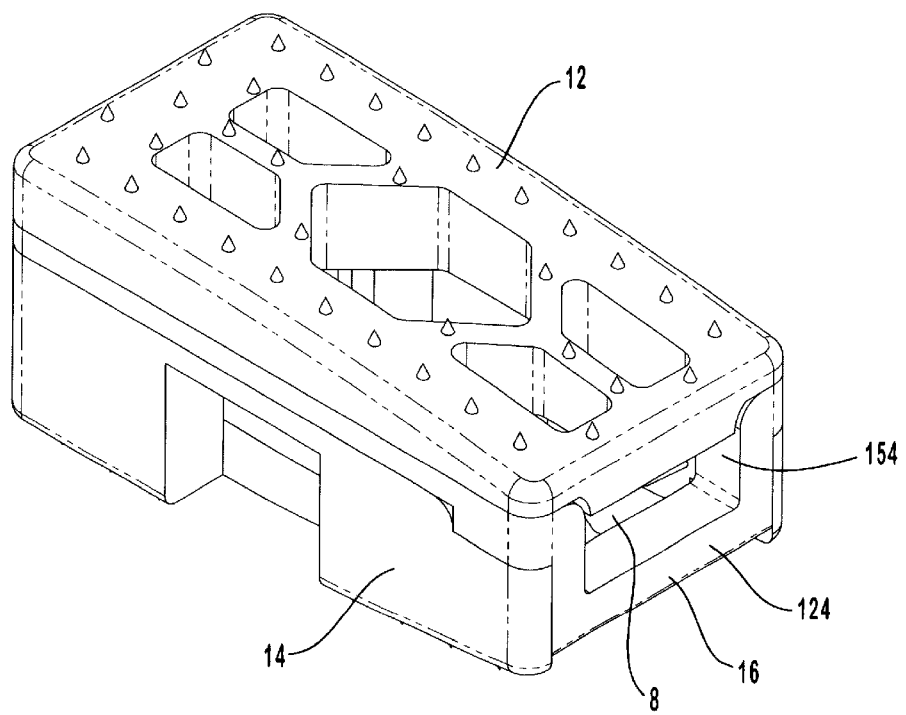
FIG. 5B is a perspective view of the fusion implant shown in FIG. 5A assembled with the reinforcing member.
Figure 6A:
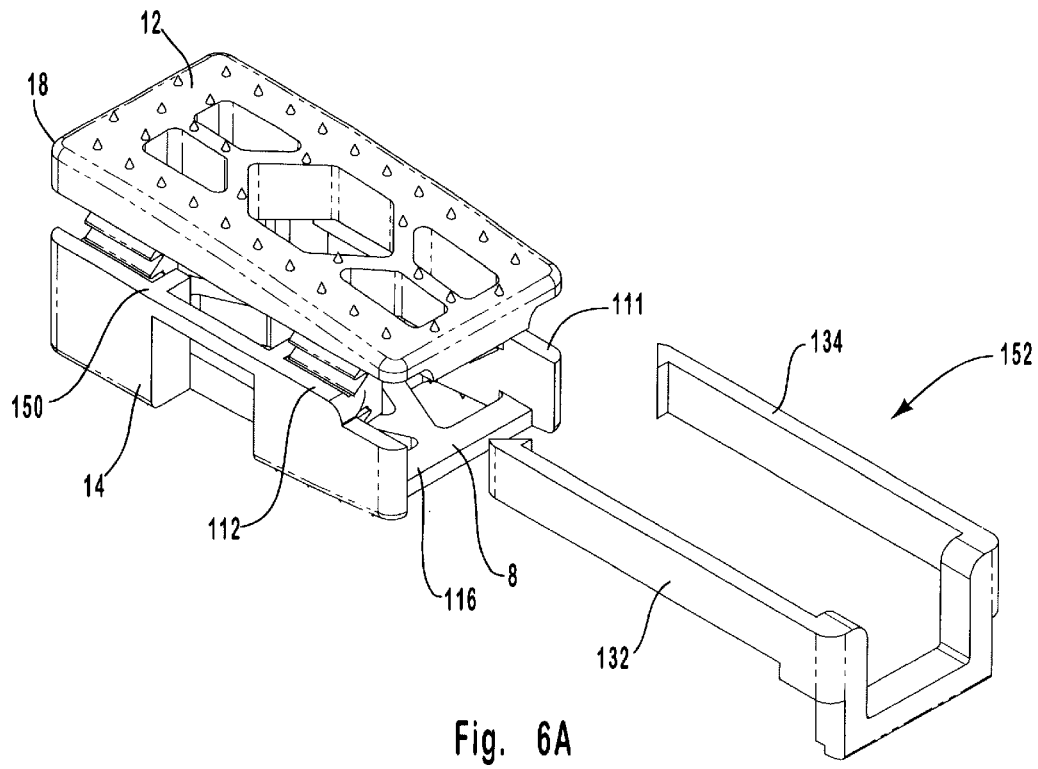
FIG. 6A is a perspective view of the fusion implant shown in FIG. 5A expanded to a greater extent to receive a larger reinforcing member.
Figure 6B:
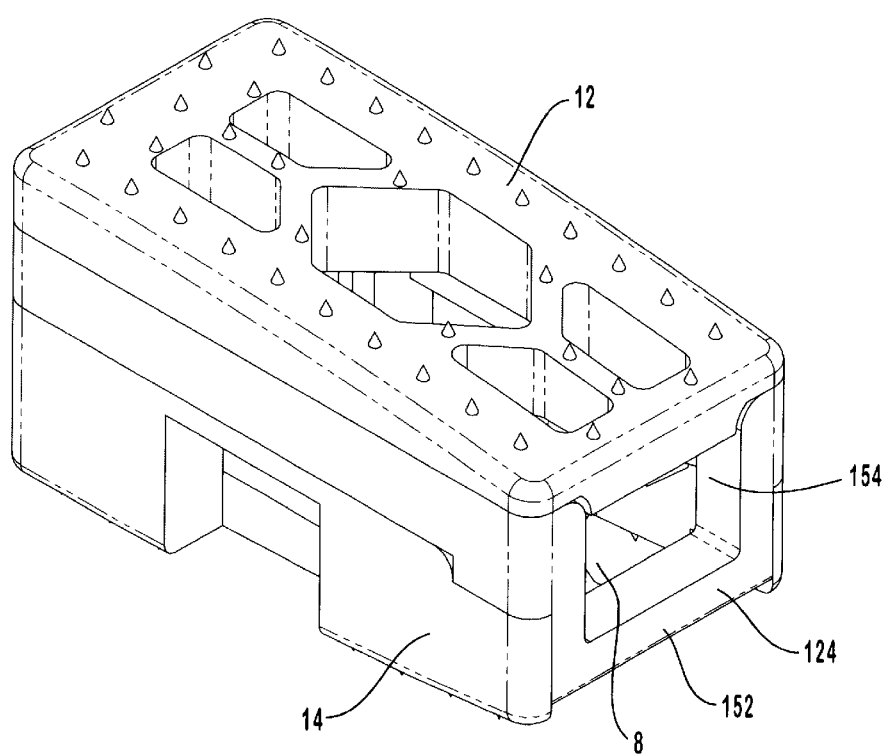
FIG. 6B is a perspective view of the fusion implant shown in FIG. 6A assembled with the larger reinforcing member.

As depicted in FIGS. 5B and 6B, the purpose of using U-shaped cantilever beam 124 is that beam 124 only covers a portion of access mouth 116. An opening 154 remains that provides communication with compartment 8. As discussed below, opening 154 can be used for feeding bone graft into compartment 8.

Each of the components of fusion implant 10 is made from a medical grade biocompatible material. In one embodiment, the components are molded from a carbon fiber reinforced polyetheretherketone polymer. In alternative embodiments, the components can be molded, cut, machined, or otherwise formed from medical grade biocompatible metals, polymers, ceramics, or other materials that have adequate strength. It is also appreciated that different components can be made from different materials. For example, the reinforcing member can be made of metal while the remainder is formed from a plastic.

Figure 7A:
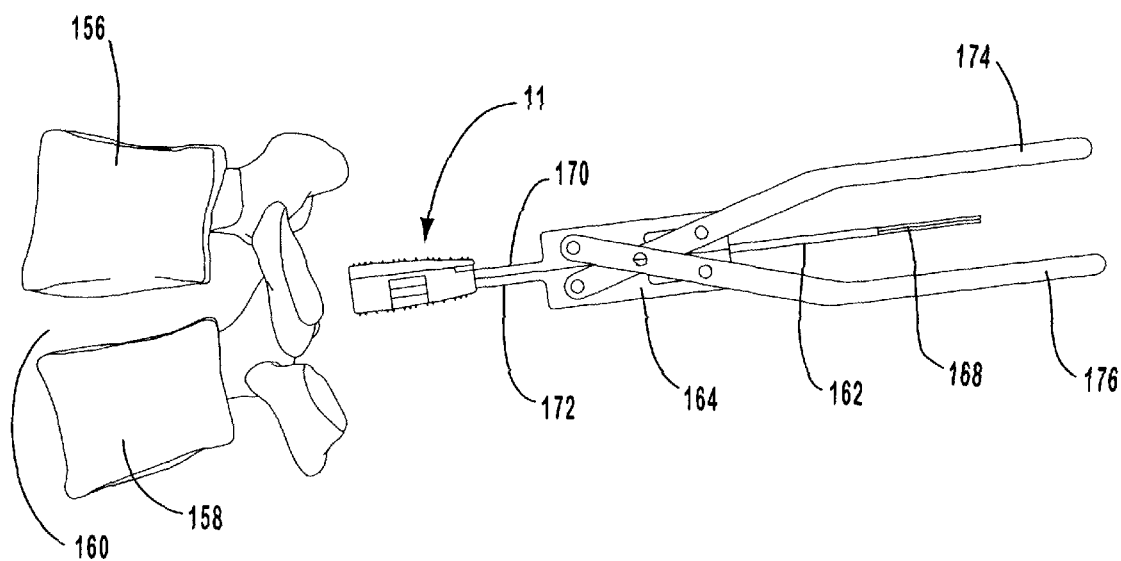
FIG. 7A is a side view of the fusion implant shown in FIG. 3A attached to an inserter and distraction tool before placement between adjacent vertebrae.

Although fusion implant 10 can be used for fusing together a variety of different bone matter together, illustrated below for purposes of example is one method of using fusion implant 10 for fusing together adjacent vertebrae in a back bone. Specifically, depicted in FIG. 7A is a pair of adjacent vertebrae 156 and 158. A posterior opening has been made through the back of the person so as to expose vertebrae 156 and 158. A disk or portion of a disk has been removed from between vertebrae 156 and 158 so that a gap 160 is formed therebetween. Because of the select vertebrae, gap 160 is wedged shaped having a wider portion that faces anteriorly towards the front of a patient and is narrower posteriorly towards the back of the patient.

To optimize fusing of vertebrae 156 and 158 while minimizing postoperative complications, a wedged shaped fusion implant having a size substantially corresponding to gap 160 should be inserted with gap 160. Because gap 160 narrows posteriorly, conventional procedures have required that if a wedged shaped implant was to be inserted within gap 160, it would have to be inserted anteriorly through the front of the patient. Inserting through the front of the patient, however, significantly complicates the procedures in that it requires the surgeon to navigate around a number organs and blood vessels. The other conventional option was to insert a flat, i.e., non-wedged shaped, fusion implant posteriorly into gap 160. Since the fusion implant was flat, however, it would not properly fit gap 160, thereby raising the specter of potential post-operative complications. As discussed below, the present invention enables the posterior insertion of a wedged shaped fusion implant into gap 160, thereby optimizing the benefits.

Figure 7B:
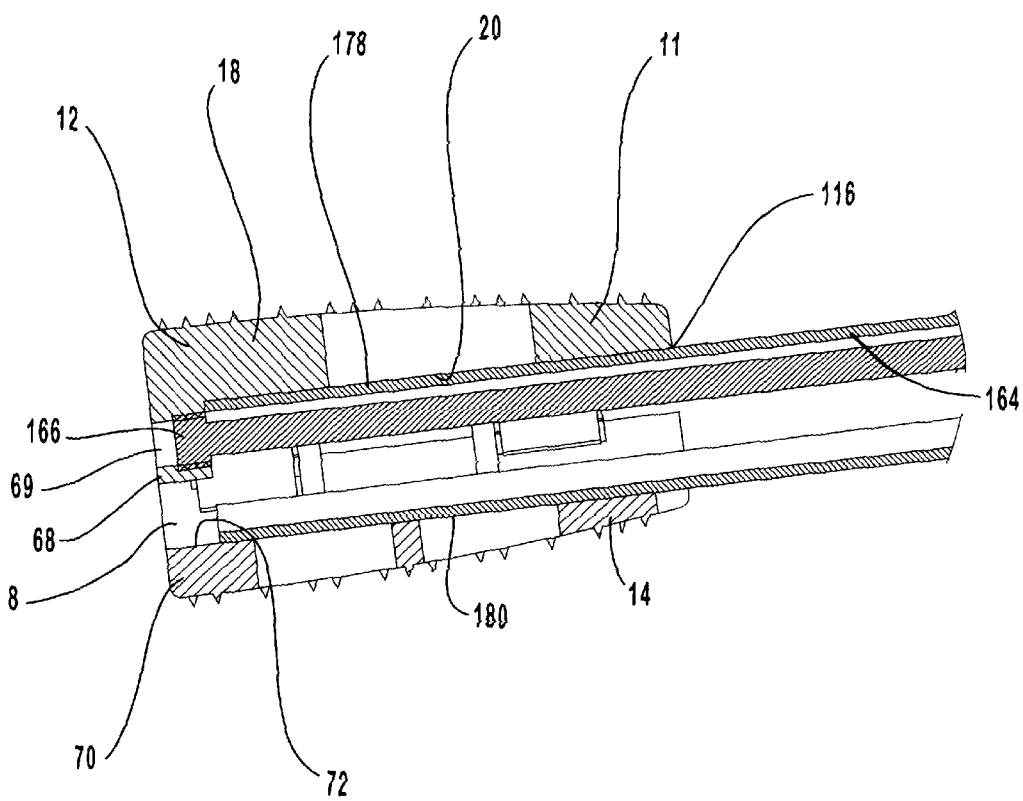
FIG. 7B is an enlarged cross section view of the fusion implant shown in FIG. 7A with the distraction tool being separated.

As depicted in FIGS. 7A and 7B, in one embodiment housing 11 of fusion implant 10 is inserted through the use of an inserter 162 and a distraction tool 164. Inserter 162 simply comprises an elongated shaft having a proximal end 166 that is inserted into access mouth 116, through compartment 8, and then screwed into threaded opening 69 in attachment flange 68. Inserter 162 also has a distal end 168 that is remotely located outside of housing 11. In alternative embodiments, it is appreciated that attachment flange 68 can be connected to base 14. Furthermore, there are a variety of alternative connection systems and methods that can be used to connect insert 162 to attachment flange 68.

In the embodiment depicted, distraction tool 164 comprises a pair of straight jaws 170 and 172 that are disposed in substantially parallel alignment. Jaws 170 and 172 are hingedly connected to a pair of handles 174 and 176 such that separation of handles 174 and 176 result in substantially constant parallel separation of jaws 170 and 172. As depicted in FIG. 7B, jaws 170 and 172 terminate in a corresponding needle nose 178 and 180, respectively. Needle noses 178 and 180 are inserted through access mouth 116 and into compartment 8 such that needle nose 178 rests against interior face 20 of cap plate 18 and needle nose 180 rests against interior face 72 of base plate 70. (It is noted that for purposes of clarity, distraction tool 164 in FIG. 7B has been expanded as discussed below with regard to FIG. 9.)

Figure 8:
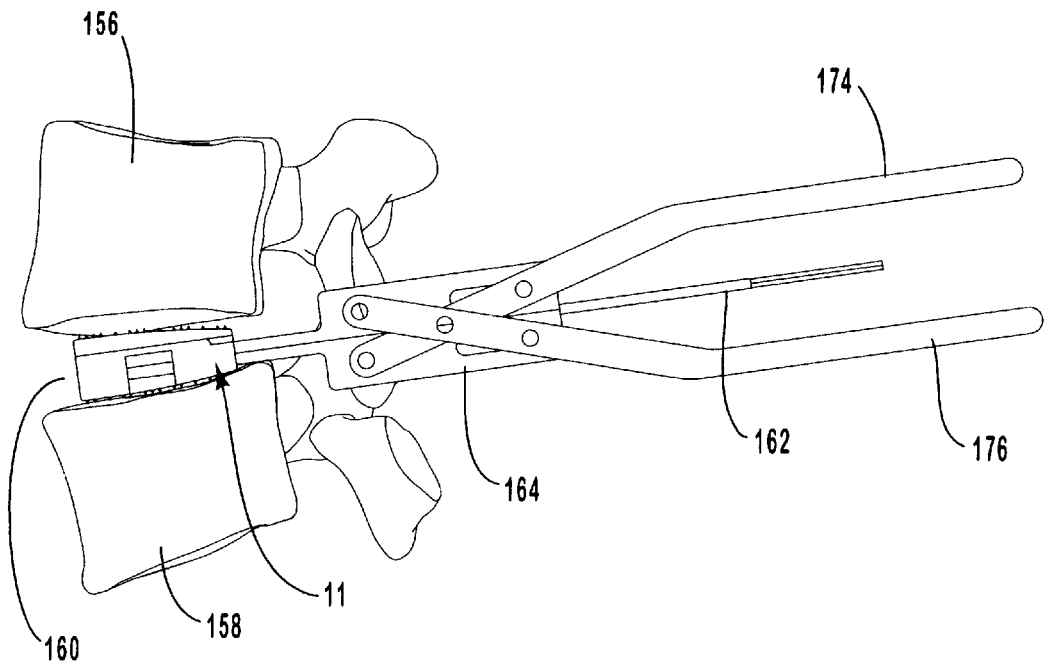
FIG. 8 is a side view of the fusion implant with inserter and distraction tool after placement between adjacent vertebrae.

In this configuration, as depicted in FIG. 8, distraction tool 164 is used to posteriorly insert housing 11 within gap 160. The enlarged distal end of housing 11 is inserted first so that the wedged shaped configuration of the housing 11 matches with the wedged shaped configuration of gap 160.

Figure 9:
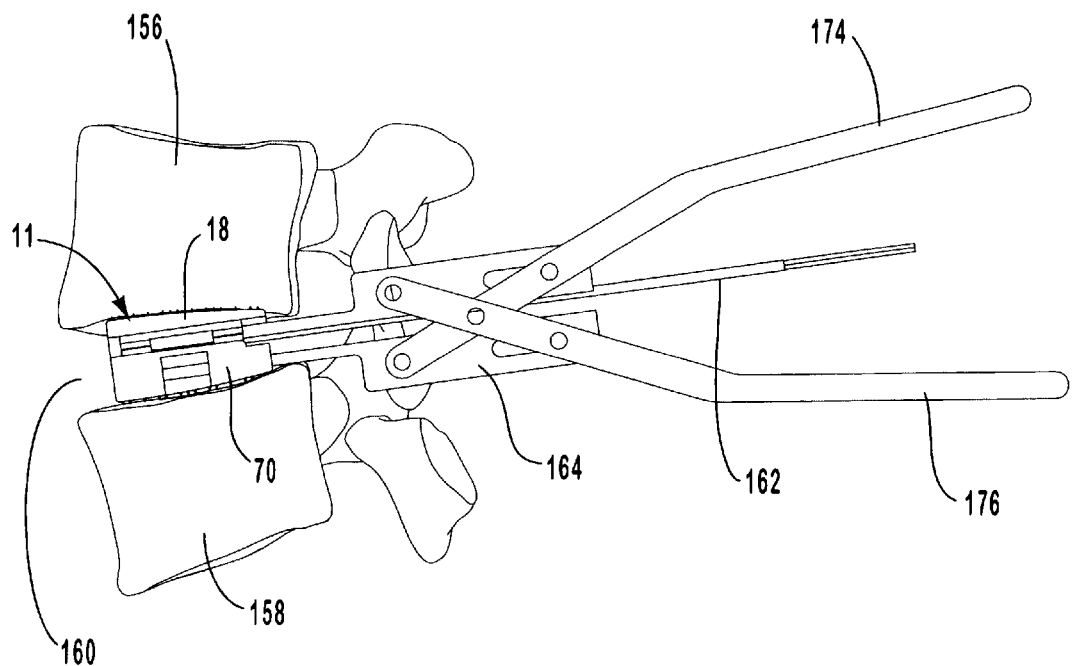
FIG. 9 is a side view of the fusion implant shown in FIG. 8 being expanded by the distraction tool.

As depicted in FIG. 9, once housing 11 is inserted within gap 160, the handles 174 and 176 of distraction tool 164 are expanded such that jaws 170 and 172 are separated. In so doing, housing 11 is also separated, i.e., cap plate 18 is further separated from base plate 70, so that cap plate 18 biases against vertebrae 156 and base plate 70 biases against vertebrae 158. Teeth 60 and 100, as previously discussed, retain housing 11 in the expanded position.

Figure 10:
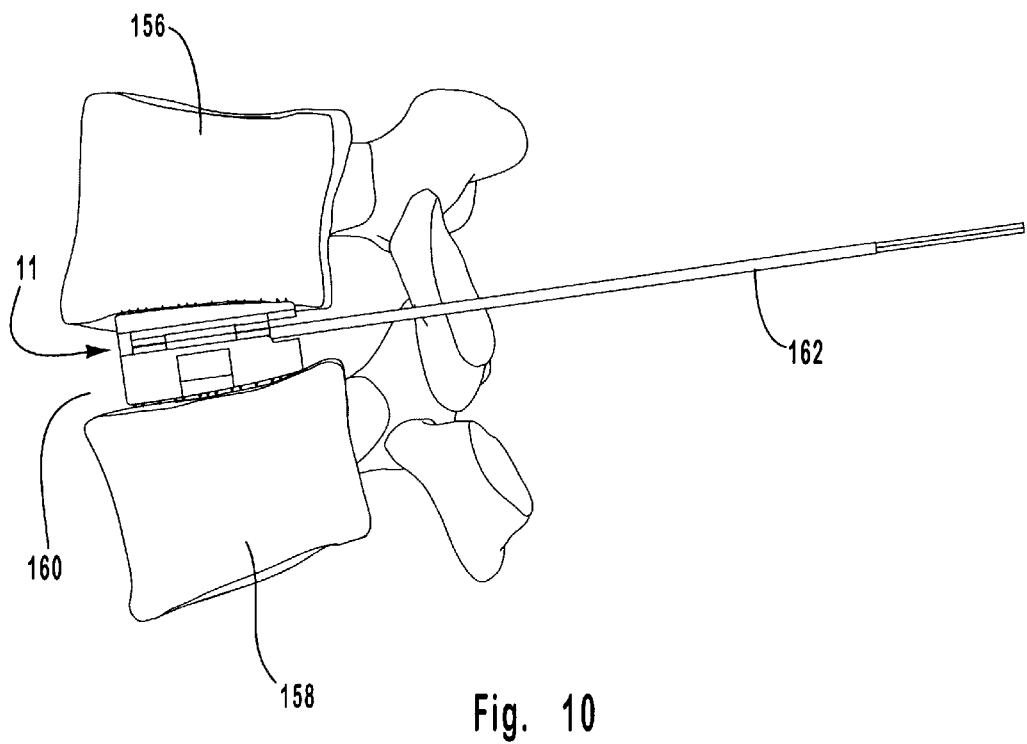
FIG. 10 is the side view of FIG. 9 with the distraction tool removed.

Once housing 11 is expanded within gap 160, distraction tool 164 is collapsed and removed from with housing 11 as depicted in FIG. 10. It is appreciated that distraction 164 can have a variety of different configuration. Virtually any form of tool can be used which can be inserted within compartment 8 and expanded. For example, not only could a number of different forms of pliers be used but other tools which expand by rotation or inflation could also be used.

Figure 11:
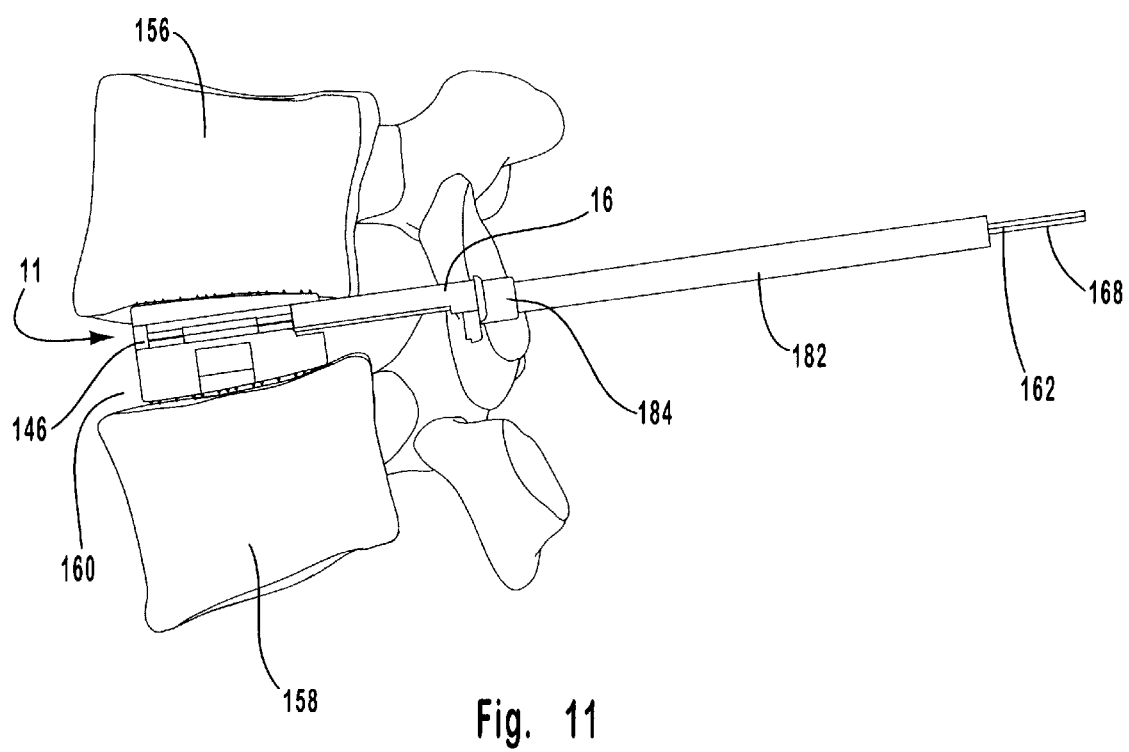
FIG. 11 is the side view of FIG. 10 with the reinforcing member and a push rod coupled to the inserter.
Figure 12:
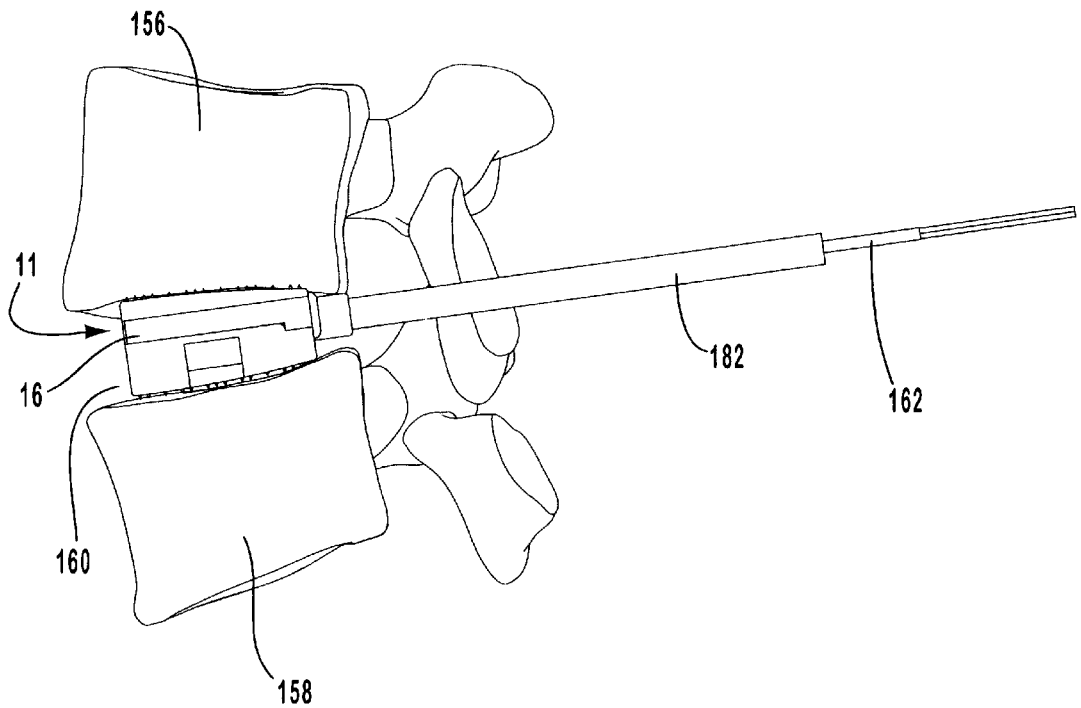
FIG. 12 is the side view of FIG. 11 with the reinforcing member being installed on the fusion implant.

Next, as depicted in FIG. 11, reinforcing member 16 is aligned with gap 146. A tubular push rod 182 is provided having an enlarged head 184. Push rod 182 is passed over the distal end 168 of inserter 162 such that enlarged end 184 is aligned with reinforcing member 16. In one embodiment, push rod 184 is removably connected to reinforcing member 16 such as by threaded engagement. In this position, push rod 182 is manually advanced over inserter 162 such that push rod 182 advances retention member 16 through gap 146. As a result, retention member 16 is secured to housing 11 as shown in FIG. 12.

Figure 13:
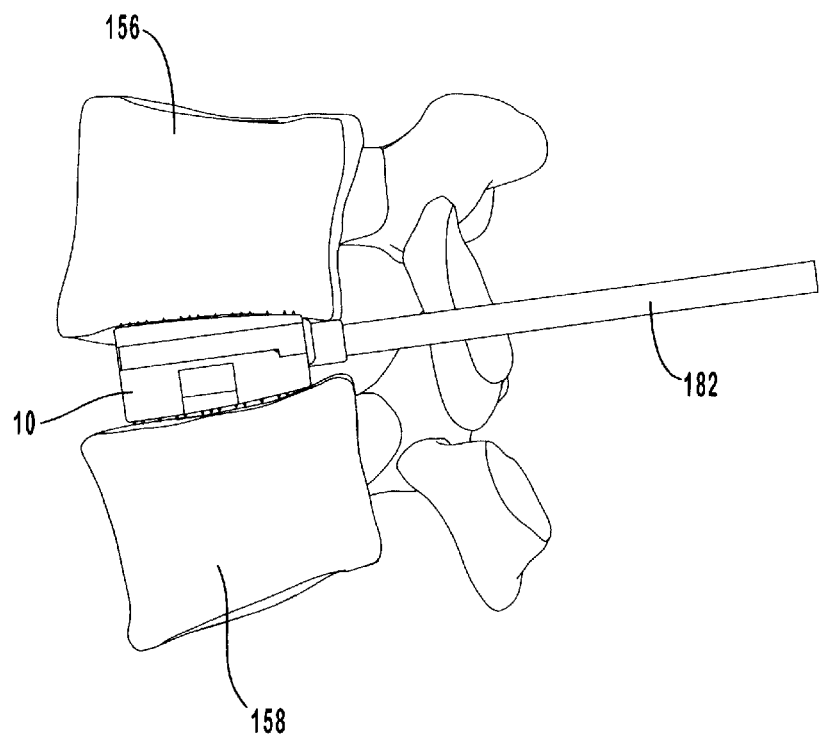
FIG. 13 is the side view of FIG. 12 with the inserter removed.
Figure 14:
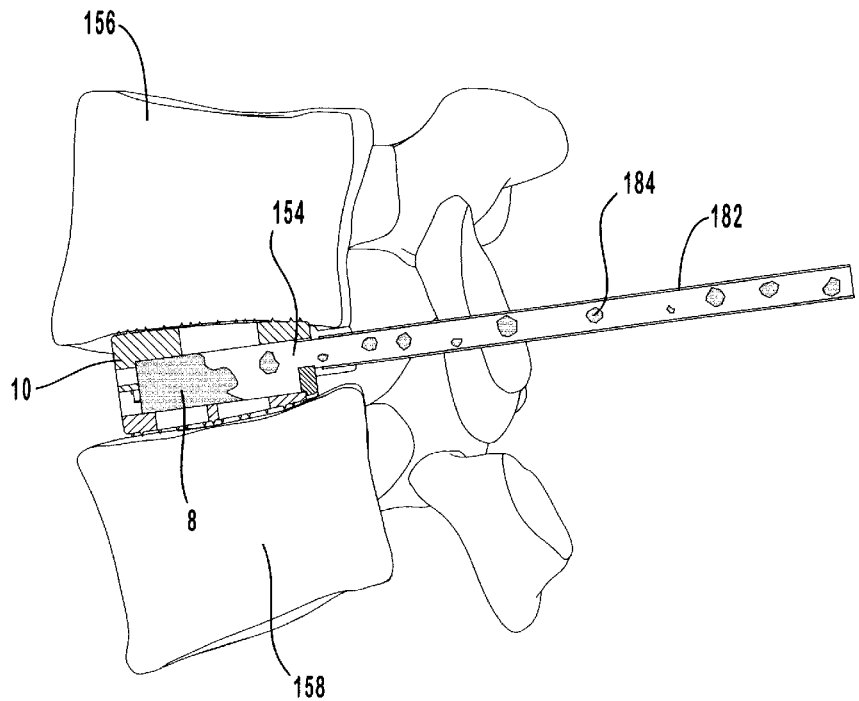
FIG. 14 the side view of FIG. 13 with the push rod in partial cut away showing the delivery of osteogenic material.
Figure 15:
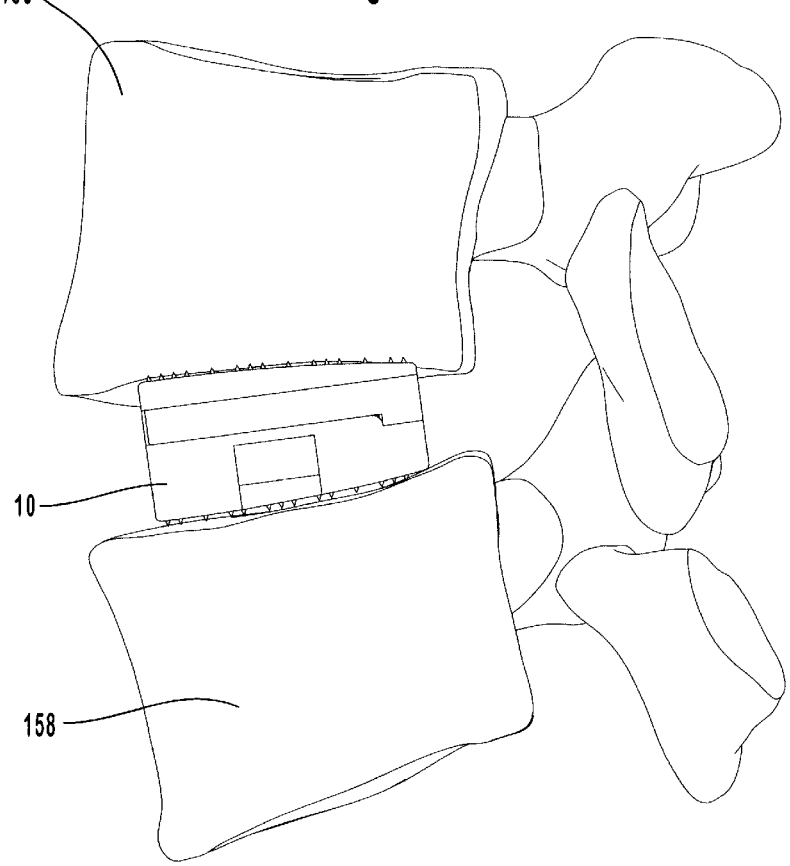
FIG. 15 is a side view of the assembled fusion implant installed in the intervertebral space.

In this position, inserter 162 is unscrewed from attachment flange 168 and withdrawn out of tubular push rod 182 as shown in FIG. 13. As depicted in FIG. 14, tubular push rod 182 is now in fluid communication with compartment 8 through opening 154. As such, an osteogenic substance 184, such as bone graft, is passed down through push rod 182 so as to pack compartment 8 therewith. Once compartment 8 is sufficiently packed with osteogenic substance 184, push rod 182 is removed as depicted in FIG. 15. Alternatively, a cap (not shown) may be delivered through push rod 182 and installed on reinforcing member 16 or within opening 154 so as to better contain osteogenic substance 184 within compartment 8.

The above process is for inserting fusion implant 10 within gap 160 on one side of a spinal cord. If required, the same above process can then be repeated for inserting another fusion implant 10 within gap 160 on the opposing side of the spinal cord.

Figure 16A:
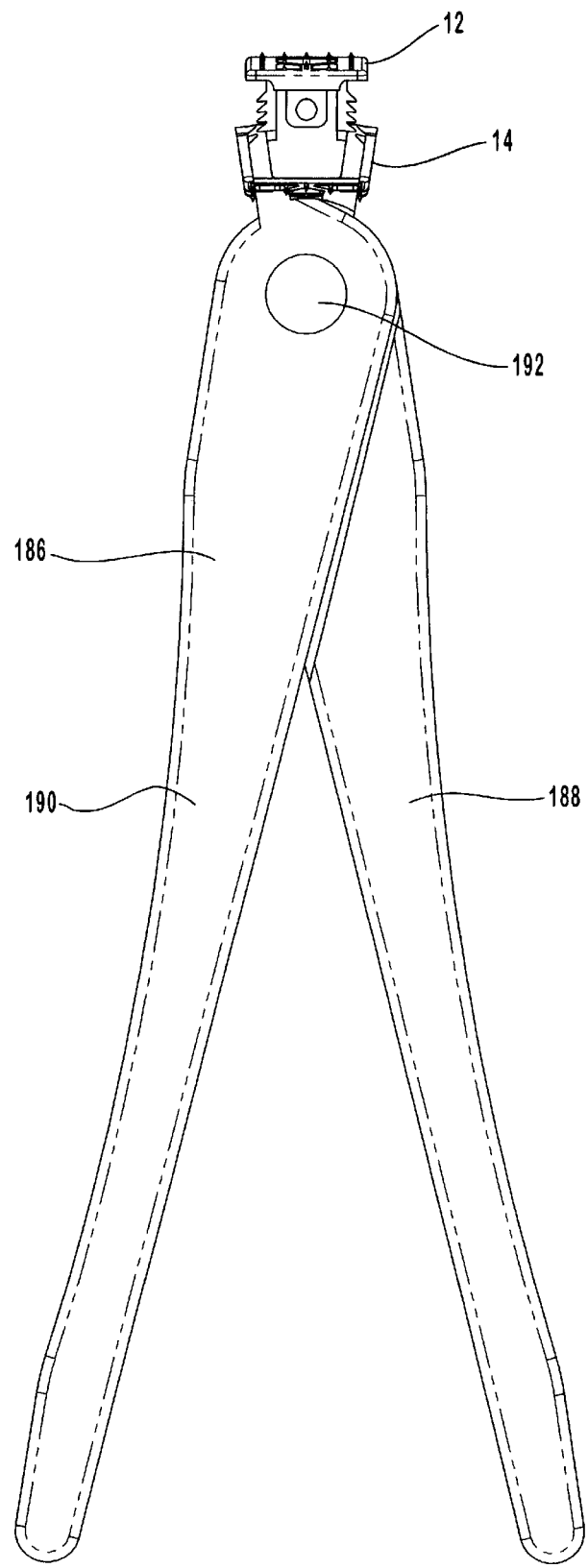
FIGS. 16A and 16B are elevated side views of expansion pliers expanding a base of the fusion implant shown in FIG. 1 for receiving a cap thereof.
Figure 16B:
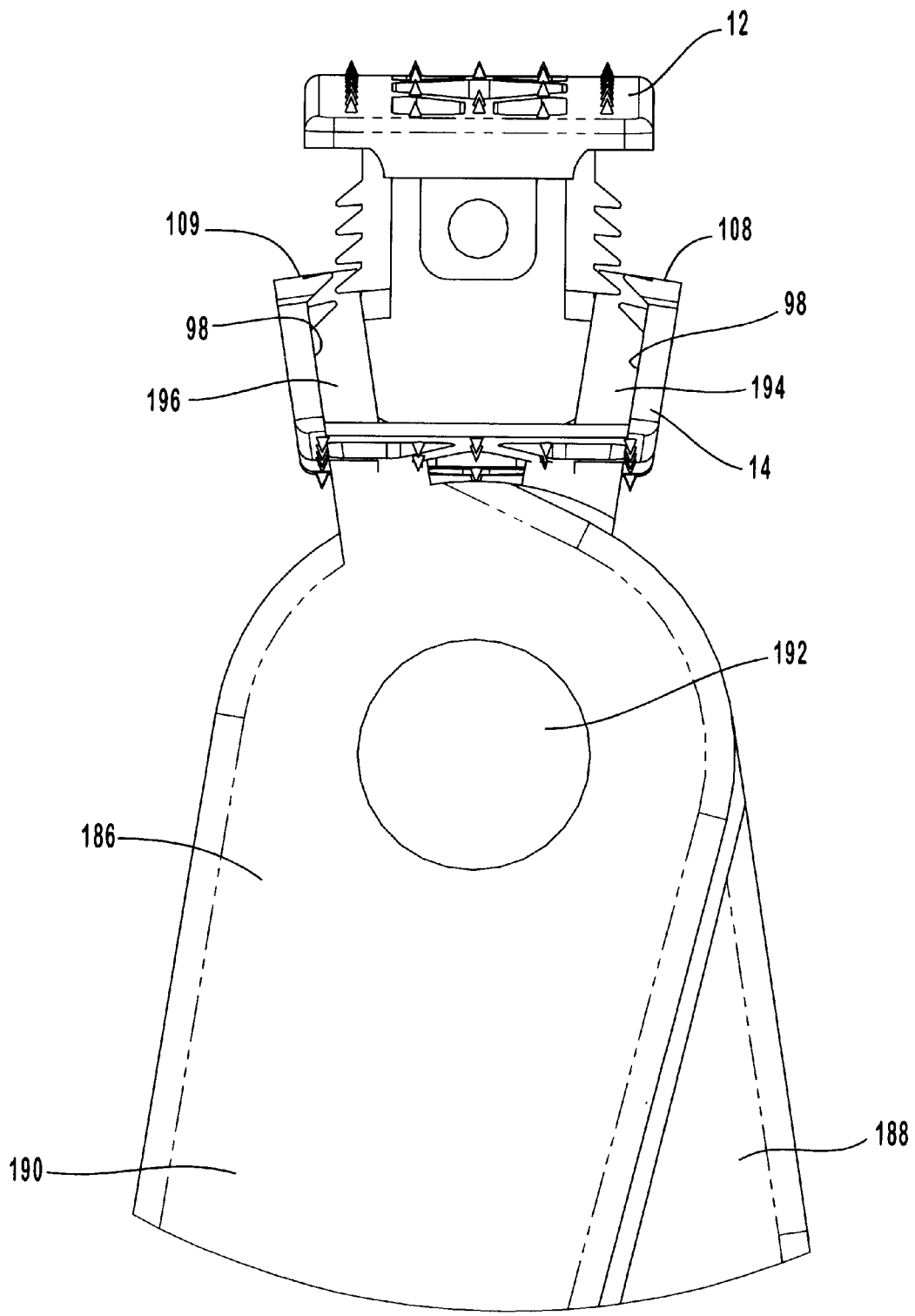

Depicted in FIGS. 16A and 16B is one method for initially attaching cap 12 to base 14. As depicted therein, expansion pliers 186 are provided comprising a pair of handles 188 and 190 that are secured together at a hinge 192. A narrow prong 194 and 196 projects from handles 188 and 190, respectively, at hinge 192. The prongs are positioned such that as handles 188 and 190 are separated, prongs 194 and 196 are also separated.

As previously discussed with regard to FIG. 2, a vertical channel 101 is formed on each side of base 14. Each vertical channel 101 extends to a location inward of braces 108 and 109. Depicted in FIGS. 16A and 16B, prongs 194 and 196 have each been received within a corresponding vertical channel 101 so that the top end of prong 194 and 196 is positioned inward of brace 108 and 109, respectively. Handles 188 and 190 have been separated so as to separate prongs 194 and 196. As prongs 194 and 196 were separated, the prongs biased against braces 108 and 109, thereby causing support members 86–89 with teeth 100 thereon to outwardly flex.

With teeth 100 outwardly flexed, support members 48–51 of cap 12 can be freely disposed inward of support members 86–89 of base 14. Expansion pliers 186 can then be collapsed and removed, thereby causing support members 48–51 to engage with corresponding support members 86–89 as previously discussed.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for fusing two adjacent bones or pieces of bone, the method comprising:
    inserting an adjustable fusion implant between two adjacent bones or pieces of bone, the fusion implant comprising a first plate and an opposing second plate with a compartment formed therebetween;
    expanding a portion of a tool inserted within the fusion implant so as to expand the fusion implant between the bones or pieces of bone;
    removing the tool from within the fusion implant; and inserting a reinforcing member between the first plate and the second plate.

2. A method as recited in claim 1, wherein the act of inserting comprises inserting the adjustable fusion implant between two adjacent vertebrae.

3. A method as recited in claim 1, further comprising removably securing a distal end of an inserter to the fusion implant prior to the act of inserting.

4. A method for fusing two adjacent bones or pieces of bone, the method comprising:
    inserting an adjustable fusion implant between two adjacent bones or pieces of bone, the fusion implant having a first plate and an opposing second plate with a compartment formed therebetween;
    expanding the fusion implant between the bones or pieces of bone so as to further separate the first plate from the second plate; and
    positioning a reinforcing member between the first plate and the second plate such that the application of a compressive force between the first plate and the second plate causes the reinforcing member to be compressed between the first plate and the second plate.

5. A method as recited in claim 4, wherein the act of expanding comprises:
    expanding at least a portion of a tool within the fusion implant so as to selectively expand the fusion implant; and
    removing the tool from within the fusion implant.

6. A method as recited in claim 4, further comprising removably securing a distal end of an inserter to the fusion implant such that at least a portion of the inserter is disposed within the compartment of the fusion implant, the inserter being secured prior to the act of inserting.

7. A method as recited in claim 6, wherein the act of positioning comprises:
    advancing a tubular push rod over a distal end of the inserter; and
    moving the push rod along the inserter so that the push rod advances the reinforcing member between the first plate and the second plate.

8. A method as recited in claim 7, further comprising:
    removing the inserter from within the push rod; and
    feeding bone graft through the tubular push rod and into the compartment of the fusion implant.

9. A method for fusing two vertebrae, the method comprising:
    forming a posterior opening through a back of a person so as to expose two vertebrae, the two vertebrae having a wedged shape gap formed therebetween that enlarges anteriorly toward a front of the person;
    inserting an adjustable fusion implant through the posterior opening and into the gap formed between the vertebrae, the fusion implant comprising a first plate and an opposing second plate and having a wedge shaped configuration that enlarges from a proximal end to a distal end, the distal end of the fusion implant being inserted first into the gap formed between the vertebrae;
    expanding the fusion implant disposed between vertebrae such that the fusion implant maintains a wedge shaped configuration; and inserting a reinforcing member between the first plate and the second plate.

10. A method as recited in claim 9, wherein the act of expanding comprises:
    expanding at least a portion of a tool within the fusion implant so as to selectively expand the fusion implant; and
    removing the tool from within the fusion implant.

* * * * *

UNITED STATES PATENT AND TRADEMARK OFFICE
CERTIFICATE OF CORRECTION

PATENT NO.    : 6,648,917 B2
DATED         : November 18, 2003
INVENTOR(S)   : Gerbec et al.

It is certified that error appears in the above-identified patent and that said Letters Patent is hereby corrected as shown below:

Column 1,
Line 55, change "in situ" to -- *in situ* --

Column 4,
Line 8, change "member:" to -- member; --
Line 10, change "member." to -- member; --

Column 6,
Line 9, change "aperature 70" to -- aperture 69 --
Line 12, change "plate 69" to -- plate 70 --

Column 9,
Line 61, after "number" insert -- of --

Signed and Sealed this

Twenty-fifth Day of May, 2004

JON W. DUDAS
*Acting Director of the United States Patent and Trademark Office*